United States Patent
Ganesan et al.

(10) Patent No.: US 7,964,215 B1
(45) Date of Patent: Jun. 21, 2011

(54) DELAYED RELEASE DOSAGE FORM

(75) Inventors: Madurai Gurusamy Ganesan, Newark, DE (US); Ramaswamy Balakrishnan, Chadds Ford, PA (US); Nutan Kumar Gangrade, Hockessin, DE (US); Steven D. Roth, Great Neck, NY (US)

(73) Assignee: Emet Pharmaceuticals, LLC, Great Neck, NY (US)

( * ) Notice: Subject to any disclaimer, the term of this patent is extended or adjusted under 35 U.S.C. 154(b) by 578 days.

(21) Appl. No.: 11/604,434

(22) Filed: Nov. 27, 2006

Related U.S. Application Data

(63) Continuation of application No. 11/338,035, filed on Jan. 24, 2006, now abandoned.

(51) Int. Cl.
*A61K 9/22* (2006.01)
*A61K 9/28* (2006.01)
*A61K 9/32* (2006.01)

(52) U.S. Cl. .................. 424/468; 424/474; 424/482

(58) Field of Classification Search ............... None
See application file for complete search history.

(56) References Cited

U.S. PATENT DOCUMENTS

| | | | | |
|---|---|---|---|---|
| 4,910,021 A * | 3/1990 | Davis et al. | ............ | 424/456 |
| 5,013,727 A | 5/1991 | Halskov | | |
| 5,171,580 A * | 12/1992 | Iamartino et al. | ............ | 424/490 |
| 5,541,170 A | 7/1996 | Rhodes et al. | | |
| 5,541,171 A * | 7/1996 | Rhodes et al. | ............ | 514/166 |
| 5,914,132 A * | 6/1999 | Kelm et al. | ............ | 424/478 |
| 6,039,975 A | 3/2000 | Shah et al. | | |
| 6,165,513 A * | 12/2000 | Dansereau et al. | ............ | 424/490 |
| 6,228,396 B1 | 5/2001 | Watts | | |
| 6,413,494 B1 | 7/2002 | Lee et al. | | |
| 6,893,662 B2 | 5/2005 | Dittmar et al. | | |
| 2002/0015735 A1* | 2/2002 | Hedden et al. | ............ | 424/488 |

OTHER PUBLICATIONS

Khan et al "A pH Dependent Colon-Targeted Oral Drug Delivery System Using Methacrylic Acid Copolymers. II. Manipulation of Drug Release Using Eudragit® L100 and Eudragit S100 Combinations," Drug Development and Industrial Pharmacy, 26(5): 549-554 (2000).*

Khan et al ("A pH Dependent Colon-Targeted Oral Drug Delivery System Using Methacrylic Acid Copolymers. II. Manipulation of Drug Release Using Eudragit® L100 and Eudragit $100 Combinations," Drug Development and Industrial Pharmacy, 26(5): 549-554 (2000)).*

Khan, et al., "A pH-dependent colon targeted oral drug delivery system using methacrylic acid copolymers, I. Manipulation of drug release using Eudragit®L100-55 and Eudragit® S100 combinations", Journal of Controlled Release, 58 (1999) pp. 215-222.

Khan, et al., "A pH-Dependent Colon-Targeted Oral Drug Delivery System Using Methacrylic Acid Copolymers. II. Manipulation of Drug Release Using Eudragit® L100 and Eudragit® S100 Combinations", Drug Development and Industrial Pharmacy, 26(5), pp. 549-554 (2000).

S.K. Jain, "Pharmaceutical Approaches to Colon Targeted Drug Delivery System", Research Projects Laboratory, Department of Pharmaceutical Sciences, Gour University, Sagar (M.P.), India (pp. 33-66 (2003).

Saffran, et al., "A New Approach to the Oral Administration of Insulin and other Peptide Drugs", Science, vol. 233, pp. 1081-1084 ((1986).

Roseman, et al., "Controlled Release of Bioactive Materials", Proceedings of the 20th International Symposium, Controlled Release Society, Inc., pp. 288-289 (1993).

Rubinstein, et al., In Vitro Evaluation of Calcium Pectinate: A Potential Colon-Specific Drug Delivery Carrier, Pharmaceutical Research, vol. 10, pp. 258-263 (1993).

Rubenstein, et al., "Colonic Drug Delivery, Enhanced Release of Infomethacin from Cross-Linked Chondroitin Matrix in Rat Cecal Content", Pharmaceutical Research, vol. 9, pp. 276-278 (1992 ).

Rubenstein, et al., "Synthesis and swelling-dependent enzymatic degradation of borax-modified guar gum for colonic delivery purposes", S.T.P. Pharma Sciences 5(1), 41-46 (1995).

Ashford, et al., "An in vitro investigation into the suitability of pH-dependent polymers for colonic targeting", International Journal of Pharmaceutics 91, pp. 241-245 (1993).

Schroeder, et al., "Coated Oral 5-AminosalicylicAcid Therapy for Mildly to moderately Active Ulcerative Colitis", The New England Journal of Medicine, pp. 1625-1629 (1987).

Ashford, et al., "Targeting Drugs to the Colon: Delivery System for Oral Administration", Journal of Drug Targeting, vol. 2, pp. 241-257 (1994).

Mackay, et al., "Colonic Delivery of Therapeutic Peptides and Proteins", Colonic Absorption and Metabolism, Human Pharmacology Institute, pp. 159-177 (1993).

Gurny, et al., Pulsatile Drug Delivery, Band 33, pp. 11-25 (1993).

* cited by examiner

*Primary Examiner* — Robert A Wax
*Assistant Examiner* — Suzanne Ziska
(74) *Attorney, Agent, or Firm* — Lucas & Mercanti, LLP

(57) ABSTRACT

The present invention is directed to a delayed release pharmaceutical composition in solid dosage form comprising a core comprised of a therapeutically effective amount of drug, e.g., mesalamine, and a pH sensitive coating comprising a mixture of two different pH sensitive polymers, the first pH sensitive polymer dissolves in an aqueous solution at a pH of about 7 or greater and the second pH sensitive polymer dissolves in an aqueous solution at a pH of about 6 or greater, wherein the weight ratio of the first pH sensitive polymer to the second pH sensitive polymer ranges from about 2:1 to about 4:1 and the percent weight gain resulting from the addition of the pH sensitive coating ranges from about 8% up to and including 15% by weight of the core, including any subcoating.

15 Claims, No Drawings

DELAYED RELEASE DOSAGE FORM

RELATED APPLICATIONS

This application is a continuation application of U.S. application Ser. No. 11/338,035, filed Jan. 24, 2006 now abandoned.

BACKGROUND OF THE INVENTION

Colon targeted delivery systems have been the subject of much research because the colon is a site for some specific diseases, such as, for example, ulcerative colitis, Crohn's disease, bowel cancer, infections and constipation and the like, which require local delivery of the drug(s) for treatment thereof. In particular, 5-amino-salicylic acid (mesalamine or 5-ASA) has been used for many years for the treatment of colonic disorders. When administered orally, mesalamine is mostly absorbed in the small intestine before reaching the colon.

In order to deliver a drug such as mesalamine to the colon selectively, a pharmaceutical composition is required to meet the following criteria: (1) the composition is not degraded or disintegrated in the upper GI tract; (2) the composition does not release the drug in the upper GI tract; (3) the composition releases the drug effectively in the colon; and (4) the composition is easy to formulate in a form suitable for loading the drug. Further, the composition preferably must be easily processed for manufacture. Various approaches have been used for oral delivery of drug(s) to the colon. These include time-dependent delivery, pH-dependent systems and delivery systems that utilize bacteria in the colon or enzymes produced by these bacteria to affect drug release.

Time release systems have been developed, such as Pulsincap® and Time Clock®, which involve a polymeric coating of a certain thickness that dissolves over time, and an outer coating that does not dissolve in the acidic environment of the stomach. This approach assumes that, while transit time is highly variable in the stomach, transit time through the small intestines is relatively constant. See Chourasia, *Pharmaceutical Approaches to Colon Targeted Drug Delivery Systems, J. Pharma. Sci.* 6(1): 33-66 (2003).

Saffran et al., *Science,* 233, pp. 1081-84 (1988) reported the use of azopolymers (i.e. polymers cross-linked with azo-aromatic groups) for colonic delivery. These are degraded by colonic bacterial azo-reductases, but are unaffected by gastric enzymes, and therefore were proposed as potential coatings for colonic delivery systems. These coatings are not ideal for a colon targeted delivery system, since release of drug depends on the presence of colonic anaerobic bacteria. Since the flora of anaerobic bacteria in the colon is variable, these polymers provide inconsistent drug delivery to the colon. Also, the safety of these polymeric coating materials is not completely established.

Site-specific delivery into the colon can also be achieved by the use of coating materials that are specifically degraded in the colonic environment by the action of microorganisms and/or the reductive environment found there. Such materials include but are not limited to azopolymers (Saffren et al., *Science*, pp. 1081-84 (1988)), amylose (Milojevic et al., Proc. Int. *Symp. Contr. Rel. Bioact. Mater.,* 20, 288, 1993), calcium pectinate (Rubenstein et al., *Pharm. Res.,* 10, 258-263, 1993), chondroitin sulphate (Rubenstein et al., *Pharm. Res.,* 9, 276-278, 1992), and modified guar gum (Rubenstein and Gliko-Kabir, *S. T. P. Pharma Sciences* 5, 4146, 1995).

Predominantly, colonic delivery has been achieved for many years by the use of pH-sensitive coatings. By raising the threshold pH at which dissolution of the coating begins, it is possible to achieve colon-specific delivery by the use of pH sensitive polymers.

The most commonly used pH-dependent coating polymers are methacrylic acid copolymers e.g., Eudragit® L100-55, Eudragit® L100 and Eudragit® S100, which dissolve at pH 5.5, 6.0 and 7.0, respectively. Eudragit® L100 and S100 are copolymers of methacrylic acid and methyl methacrylate, respectively. The ratio of free carboxyl groups to ester groups is approximately 1:1 in Eudragit® L100 and 1:2 in Eudragit® S 100.

The pH-dependent systems exploit the generally accepted view that pH of the human gastrointestinal (GI) tract increases progressively from the stomach (pH 1-3) to the small intestine (pH 5-7) to the colon (pH 7-8). See Ashford, et al., *Journal of Drug Targeting* 2, pp. 241-58 (1994). Taking advantage of the highest pH value of the colon, the dosage form containing the active drug in a core is coated with pH-dependent material, which dissolves at the pH of the colon.

U.S. Pat. Nos. 5,541,171 and 5,541,170 describe an orally administered composition containing mesalamine and coated with a methacrylic acid copolymer that only dissolves in colonic-intestinal juices above a pH of 7 (Eudragit® S100). But it has been reported that, because the colonic pH of certain patients fails to reach a pH of 7 or because of a fast transit time in certain patients, embodiments of these patents fail to dissolve completely in the GI tract, with patients observing intact tablets in their stools. See, e.g., Schroeder et al., *New Eng. J. Med.* 317, 1625-29 (1987); Ashford et al., *Int. J. Pharm,* 91, pp. 241-245 (1993).

The present inventors have found a system that does not degrade, disintegrate or release the drug, e.g., mesalamine, in the upper GI tract, but instead releases it in the ileum and colon. Moreover, it is easy to formulate and easy to manufacture. In addition, the system developed is a delayed release composition, which slowly releases drug in aqueous media having a pH 6.5 to 6.8, and which quickly releases drug in media having a pH of 7.0 or more. More specifically, using the present invention in the three stage dissolution test discussed hereinbelow, about 10% to about 60%, and more preferably about 20% to about 50%, of the drug by weight is released at a residence time of about 2 hours at a pH of 6.8, while at a pH of less than 6.5, the drug is released slowly, if at all, at a rate of less than about 20% by weight during the same residence time, while at a pH of 7.2 or more, the drug is released very rapidly (greater than about 80% by weight) at a residence time of 2 hours.

SUMMARY OF THE INVENTION

It is an object of this invention to design a pharmaceutical composition for oral administration which slowly releases drug in media having a pH of 6.5 to 6.8, and which quickly releases drug in media having a pH of 7.0 or more. Preferably, in a three stage dissolution test, wherein the first stage is 2 hours in 0.1N HCl (100 rpm), and the second stage is one hour in solution buffered to a pH of 6.0 (100 rpm), drug release in the third stage (50 rpm) is low (e.g., less than about 20%) for at least two hours in media buffered to a pH of 6.5 or less, drug release is generally more substantial (e.g., about 10% to about 60% and preferably about 20% to about 50%) at two hours in media buffered to a pH of 6.8, and drug release is nearly complete (e.g., greater than about 80%) at two hours in dissolution media buffered to a pH of 7.2 or more. For purposes of the amount released, the term "about" means plus or minus 5%.

The present invention provides a delayed release pharmaceutical composition for oral administration comprising a core containing drug, e.g., mesalamine, and a pH-sensitive coating comprising a mixture of at least 2 different polymers: a first pH sensitive polymer which dissolves at a pH of about 7 or more (e.g., Eudragit® S100) and a second pH sensitive polymer which dissolves at a pH of about 6 or more (e.g., Eudragit® L100), wherein the ratio of the first pH sensitive polymer to the second pH sensitive polymer (e.g., Eudragit® S100 to Eudragit® L100) in the coating ranges from about 2:1 to about 4:1, and the thickness of the pH-sensitive coating containing the two polymers, in terms of coating weight gain, ranges from about 8% up to and including 15%. Preferably the coating weight gain ranges from about 10% up to and including 15%.

DETAILED DESCRIPTION OF THE PRESENT INVENTION

An embodiment of the present invention is directed to a delayed release oral dosage form of a medicament comprising a core comprising mesalamine coated with a coating composition comprising the mixture of the two aforementioned pH sensitive polymers within a specified weight ratio.

As used herein, the terms "medicament", "drug", "therapeutic", "pharmaceutical", "active ingredient" or "active agent" are synonyms and can be used interchangeably.

As used herein, the term "core" refers to the pharmaceutical composition which contains the active ingredient and any other subcoating therein but which excludes the coating of the present invention comprising a mixture of the two pH sensitive polymers, as defined herein, and any coating over the coating comprising the mixture of the two pH sensitive polymers.

The term "delayed release", for the purpose of the present invention, means that the therapeutically active agent, medicament or drug, e.g., mesalamine, is not released from the pharmaceutical composition immediately, but is instead released at a time when the therapeutically active agent, medicament or drug reaches the targeted site.

The present formulation preferably comprises a pharmaceutical composition in "unit dosage form". The term "unit dosage form", as employed herein, refers to a physically discrete unit suitable as unitary dosage to mammals, with each unit containing a predetermined quantity of active agent, e.g., mesalamine, to provide the desired effect in the patient being treated.

The pharmaceutical composition of the present invention is a solid. Thus, it is in the form of tablets, spheroids (or beads), microspheres, hard capsules, soft capsules, seeds, pellets or other multi-particulate solid dosage form, in order to obtain a desired delayed release of the active agent; e.g., mesalamine. Granules, spheroids, pellets and the like can be presented in a capsule or in another suitable unit dosage form. If the solid form is a tablet, the tablet can be any suitable shape, such as round, spherical, oval, concave, bi-concave, hemispherical, or any polygonal shape, such as square, rectangular, pentagonal, hexagonal, and the like. The preferred solid dosage form is a tablet.

The "patient" being treated, as used herein, is a mammal. By "mammal", it is meant vertebrae of the class Mammalia that is characterized by possession of hair and mammary glands. Examples include, inter alia, dog, cat, horse, pig, goat, cow, human being, mice, rat, donkey, and the like. The preferred species of mammal is human.

The core formulation of the present invention contains the active pharmaceutical ingredient, e.g., 5-amino-salicylic acid (5-ASA or mesalamine). It is present in therapeutically effective amounts. "Therapeutically effective amounts", as used herein, refers to the amount of therapeutically active drug, e.g., mesalamine, which is present in the pharmaceutical composition, is in sufficient concentration to provide the desired local or systemic effect and performance at a reasonable benefit/risk ratio attending any medical treatment. Thus, the active agent, e.g., mesalamine, is present in sufficient amounts to provide a positive modification of the condition to be treated but in low enough amounts to avoid serious side effects, within the scope of sound medical judgment. A therapeutically effective amount will depend upon several factors, including but not limited to, the condition being treated, the age and physical condition of the patient being treated, the severity of the condition being treated, the duration of the treatment, and the like. The physician treating the patient can determine the therapeutically effective amount of active agent easily. It is preferred, however, that the active agent, e.g., mesalamine, is present in the pharmaceutical composition in amounts ranging from about 0.5% to about 95% by dry weight of the pharmaceutical composition. The core may also contain excipients, i.e., inactive ingredients that are well known to one of ordinary skill in the art, such as diluent(s), binder(s), disintegrant(s), lubricant(s) and glidant(s).

As used herein, the term "excipient" means any component admixed with or co-incorporated with the active agent. Excipients may act to facilitate incorporation of the active agent into the substrate, modify the release of the active agent from the substrate, stabilize the active agent, enhance absorption of the active agent, enhance tableting, increase the bulk of the pharmaceutical composition, and the like. Excipients are safe for their intended use at the levels employed in the formulation and are compatible with the active agent. The combination of active agent and excipient is selected according to criteria well known to those skilled in the art. It is within the purview of one of ordinary skill in the art to determine the type of excipient to be utilized in combination with the active agent as well as to determine how much excipient is to be added and the objective that the skilled artisan wishes to achieve by adding the same.

The core is coated with the pH sensitive coating comprising the mixture of the two polymers defined herein. The pH-sensitive coating contains a first pH sensitive polymer, which readily dissolves in aqueous solutions, e.g., water or aqueous buffer at a pH of about 7 or more. It preferably dissolves in aqueous solution at a pH of about 7; for example, it begins to dissolve in an aqueous solution at a pH between about 6.8 to about 7.2. It is substantially insoluble in aqueous solution at a pH of less than about 6.5. Any polymer having this solubility characteristic may be used as the first pH sensitive polymer. An example of a pH sensitive polymer that dissolves at a pH of 7.0 is Eudragit® S 100. It is an anionic copolymer derived from methacrylic acid and methyl methacrylate with a ratio of free carboxy groups to ester groups of approximately 1:2. Preferably, it has a mean molecular weight of greater than about 100,000 daltons, e.g., about 135,000 daltons. It is currently commercially available from Rohm Tech.

The second pH sensitive polymer used in the coating dissolves in an aqueous solution, e.g., water, or aqueous buffer at a pH of about 6 or more. In other words, below about a pH of about 5.5, it is substantially insoluble in water, while at a pH above 6.0, it is completely soluble e.g., it begins to dissolve at a pH of about 5.8 or more. Any polymer having this solubility characteristic may be used as the second pH sensitive polymer. An example of such a pH sensitive polymer is Eudragit® L-100.

Eudragit® L-100 is an anionic copolymer derived from methacrylic acid and methyl methacrylate with a ratio of free carboxy groups to ester groups of approximately 1:1. Preferably it has a mean molecular weight of greater than about 100,000 daltons, e.g., about 135,000 daltons. It is commercially available from Rohm Tech.

As described herein, the weight ratio of the first pH sensitive polymer to the second pH sensitive polymer ranges from about 2:1 to about 4:1. It is preferred that the weight ratio ranges from 2:1 to 4:1, inclusive. In an embodiment of the present invention, the weight ratio of the first pH sensitive polymer to the second pH sensitive polymer ranges from about 2:1 to about 3:1, and more preferably from 2:1 to 3:1, inclusive. In another embodiment, the weight ratio ranges from about 3:1 to about 4:1 and more preferably from 3:1 to 4:1, inclusive.

The weight gain of the pharmaceutical composition containing active ingredient attributable to the aforementioned coating added onto the core (dry weight) ranges from about 8% up to and including 15% by weight of the core including any subcoating thereon. The "weight gain", as used herein, refers to the weight gain relative to the core, including any subcoating thereon, when the pH sensitive coating is added thereto. It is calculated by dividing the weight of the solid pharmaceutical composition coated with the pH sensitive coating by the weight of the solid pharmaceutical composition, including the core and any subcoating thereon, absent the pH sensitive coating. If there is an outer coating overlaying the pH sensitive coating in the pharmaceutical composition, the weight of the outer coat is not included in the calculation (neither in the numerator or denominator).

The weight gain attributable to the addition of the pH sensitive coating ranges preferably from about 10% up to and including 15% by weight and more preferably, from about 10% up to and including 15% by weight.

As defined herein the pharmaceutical composition of the present invention may contain more than one subcoating. However, as defined herein, it is preferably the outermost coating of the composition that comprises the pH sensitive coating, as defined herein.

The pH sensitive coating may also contain plasticizers. A plasticizer enhances the elasticity of the coating material. It may be an aqueous plasticizer or non-aqueous plasticizer. Appropriate plasticizers include polyethylene glycols, propylene glycols, dibutyl phthalate, dibutyl sebacate, diethyl phthalate, tributyl citrate, tributyrin, butyl phthalyl butyl glycolate, triacetin, castor oil and citric acid esters, e.g., triethyl citrate or acetyl triethyl citrate and the like. If present, the pH sensitive coating material comprises from about 0% (but greater than 0%) to about 50% by weight of a plasticizer, and more preferably from about 5% to about 25% by weight and most preferably from about 5% to about 10% by weight of the pH sensitive coating.

The pH sensitive coating may also include an anti-tack agent or glidant, such as talc, silica or gylceryl monostearate, and the like.

The pH sensitive coating as well as the core, including any subcoating thereon, may additionally contain coloring agents, preservatives (e.g., methyl parabens), flavorants, artificial sweeteners, anti-oxidants and the like.

The pharmaceutical composition, as indicated hereinabove, may also have one or more subcoats lying underneath the pH sensitive coating. As defined herein, the subcoat refers to the coatings between the pH sensitive coating and the drug matrix containing the active ingredient. The subcoat is preferably a film forming material which does not have a substantial effect and more preferably, no measurable effect on the release of the active ingredient from the core. The subcoat, if present, is present in amounts ranging from about 1 to about 5% by weight of the core. Preferably, the subcoating comprises from about 2% to about 3% of the core. The subcoat, if present, may be functional. For example, it may be employed to provide a substrate for the pH sensitive coating. If the subcoat modifies the release profile, it modifies it very slightly, the delayed release of the composition being substantially attributable to the mixture of two pH sensitive polymers in the pH sensitive coat, as described hereinabove, which, as defined herein, is preferably the outer coating of the present invention. However, there may be additional coatings overlaying the pH sensitive coating as defined herein. Preferably, any coating overlaying the pH sensitive coating of the present invention will not substantially, if at all, affect the release of the drug from the pharmaceutical composition of the present invention.

The polymeric film former that can be utilized is water-soluble or it can be water insoluble. Examples thereof that may be employed include, but not limited to, acrylic polymers, cellulose polymers and cellulose derivatives. Preferred polymers include hydroxypropylcellulose, hydroxypropylmethylcellulose, hydroxypropylmethylcellulose phthalate, methylcellulose, cellulose acetate, cellulose acetate phthalate, ethylcellulose, polyvinyl alcohol and polyvinylacetate phthalate. The most preferred polymeric film former is Opadry® (a form of hydroxypropylmethylcellulose that does not substantially affect the release of the drug). Although the pharmaceutical composition of the present invention may contain no subcoat, it preferably contains one subcoat.

The pH sensitive coating is applied to the core by conventional techniques. It may be applied to the core by dissolving or suspending the pH sensitive polymers in a suitable medium; such as water, methanol, ethanol, isopropanol, acetone, methyl ethyl ketone, methylene chloride, ethylene chloride, ethyl acetate, and the like or mixture thereof, and the resultant solution or suspension may be sprayed onto the core or subcoating on the core by conventional means to uniformly coat the core, followed by drying the composition with the coating thereon sufficiently with an air flow and screening.

Coating may be effected using fluidized bed equipment, perforated pans, a regular pharmaceutical pan, compression coating, and the like by continuous or short spray methods or by drenching, or by other techniques known to one of ordinary skill in the art.

The coating is applied so as to rapidly contact and substantially uniformly coat the core. It is preferred that the coating composition of the pharmaceutical composition is substantially an uniform thickness around the core.

The subcoat, if any, is applied prior to the application of the pH sensitive coating. It is applied by techniques known in the art in a manner similar to the way in which the pH sensitive coat is applied.

Any outer coating over the pH sensitive coat is applied after the application of the pH sensitive coating. It is applied by techniques known in the art in a manner similar to the way in which the pH sensitive coat is applied.

The pharmaceutical composition of the present invention in which the active ingredient is mesalamine is preferred. This pharmaceutical composition is useful for the treatment of colitis, e.g., ulcerative colitis. The mesalamine therein is present in therapeutically effective amounts, as defined herein.

The present composition may also contain one or more active ingredients listed hereinbelow in the core. In this embodiment, it is preferred that at least one of the active ingredients is mesalamine.

The above illustrates an example of preparing a pharmaceutical composition comprising mesalamine as the active ingredient. The drug delivery technology of this invention, however, may be used to deliver various active ingredients to the lower GI tract for the treatment of colonic and intestinal diseases, such as ulcerative colitis and Crohn's disease, including aminosalicylates, such as mesalmine, sulfasalazine, olsalazine and balsalazide; corticosteroids, such as prednisone, hydrocortisone and budesonide; immunomodulators, such as azathioprine, 6-mercaptopurine, cyclosporine and methotrexate; antibiotics such as metronidazole and ciprofloxin; and other active agents such as infliximab, tacrolimus, mycophenolate mofetil, heparin, omega-3 fatty acids, nicotine and the like.

The present invention is also applicable to any active ingredient for release in the colon, i.e., any colon-specific drug delivery system.

As used herein the term "colon-specific drug delivery system" and similar terms mean devices and methods for oral administration that release biologically active ingredients in the colon without substantial release into the upper gastrointestinal tract.

As used herein, the term "drug" or "active agent" or any other similar term means any chemical or biological material or compound suitable for administration by the methods previously known in the art and/or by the methods taught in the present invention, that induces a desired biological or pharmacological effect, which may include but is not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anaesthetic effect, or it may by systemic. By the method of the present invention, both ionized and nonionized drugs may be delivered, as can drugs of either high or low molecular weight.

Therapeutic agents suitable for incorporation into dosage forms of the present invention are those for which release in the colon is therapeutically advantageous. These include therapeutic agents useful for topical treatment of diseases of the colon such as constipation, diarrhea, irritable bowel syndrome (IBS), Crohn's disease, ulcerative colitis, carcinomas, and infection in which systemic absorption of the therapeutic agent is neither required nor desired. These include laxatives such as picosulfate and sennosides, anti-diarrheals such as loperamide, nonsteroidal anti-inflammatory drugs and steroids, such as mesalamine, described hereinabove, hydrocortisone, prednisolone, prednisolone phosphate, prednisolone metasulpho-benzoate sodium, prednisolone sodium phosphate, glucocorticoids such as dexamethazone, antimicrobials and antiparasitic agents such as erythromycin, chloroquine, iodochlorhydroxyquin, disodohydroxyquin, neomycin and tetracyclines, especially these effective against anaerobic microbes such as methotrexate, immunosuppressants such as cyclosporin A, and chemotherapeutics for treatment of carcinomas, and the like.

Certain therapeutic agents, particularly peptides and proteins, are subject to lumenal degradation in the stomach and small intestine. The colon may be a preferable site of absorption for such compounds since lumenal enzymatic activity is less in the colon (M. Mackay and E. Tomlinson, in Colonic Drug Absorption and Metabolism, P. R. Bieck, ed., Marcel Dekker, Inc., New York, Basel, Hong Kong, 137-158 (1993)). Peptides and proteins that may exhibit improved systemic bioavailability benefit when released in the colon include calcitonin, insulin, and human growth hormone. In certain cases, the peptide or protein may be formulated with a system than enhances the absorption of the macromolecule (M. Mackay and E. Tomlinson, in Colonic Drug Absorption and Metabolism, P. R. Bieck, ed., Marcel Dekker, Inc., New York, Basel, Hong Kong, 137-158 (1993)).

Colonic release is also desirable for systemic absorption of therapeutic agents for which peak systemic concentrations and pharmacological activity are desired at time significantly delayed from the time of oral administration. This is particularly advantageous for conditions such as asthma, arthritis, inflammation, coronary infarction, and angina pectoris, which are susceptible to diurnal rhythms (B. Lemmer, in Pulsatile Drug Delivery, R. Gurny, H. E. Junginger, and N. A. Pepas, eds, Wissenschaftliche Verlagsesellschaft mbH, Stuttgart, 11-24 (1993)). Drugs for which daily variations in their effects have been reported in clinical studies include cardiovascular drugs such as theophylline, minor tranquiller drugs such as ibuprofen, indomethacin, flurbiprofen, naproxen, and piroxicam, and H2-blockers such as cimetidine and ranitidine.

As used herein the plural denotes the singular and vice versa.

Unless indicated to the contrary, the term "weight", as used herein, refers to the dry weight. Moreover, unless indicated to the contrary, the weight of the pharmaceutical composition includes the dry weight of the core, including any subcoat and the pH sensitive coating.

As used hereinbelow, "SD" refers to standard deviation.

The following non-limiting examples are provided to illustrate the present invention:

EXAMPLE I (Core Composition)
Cores were manufactured with the following composition:

| Material | Amount Per Tablet (mg) | % Total |
|---|---|---|
| Mesalamine | 400.0 | 80.00 |
| Lactose Monohydrate (fast flo ®) | 57.5 | 11.50 |
| Providone K-30 | 15 | 3.00 |
| Sodium Starch Glycolate (intra granular) | 5 | 1.00 |
| Sodium Starch Glycolate (extragranular) | 15 | 3.00 |
| Colloidal Silicon Dioxide (Cab-O-sil) | 2.5 | 0.50 |
| Magnesium Stearate | 5 | 1.00 |
| Purified Water, USP | N/A | q.s. |
| Total | 500.00 | 100.00 |

About 3200 grams of mesalamine, about 460 grams of lactose and about 40 grams of intra-granular sodium starch glycolate were mixed for 5 minutes in a PMA-25 granulator at about 300 to 400 rpm. About 800 grams of a 15% solution of povidone was then added and granulation continued for an additional 5 to 10 minutes with the chopper set to a low speed.

The granulation was dried at 50 degrees C. for about 15 hours and milled and sieved. About 20 grams of silicon dioxide was added, and the granulation was milled and screened. Then the granulation was put in a PK-V blender and about 120 grams of extra-granular sodium starch glycolate was blended into the mixture for 10 minutes. About 40 grams of magnesium stearate, previously screened, was blended into the mixture for 5 minutes. The granulation was compressed into tablet cores using a Minipress II rotary tablet machine using either 7/16" or 13/32" tooling to a hardness of about 20 kp.

Example II

2:1 Coating at 8% and 11%

A 3% (w/w) sub-coat containing a mixture of 150 grams Opadry and 850 grams water was applied to the cores of Example I. (Approximately, inlet air temp. 50° C., exhaust temp. 45° C., bed temp. 42° C., fan speed 200 cfm, pan speed 8 rpm, air pressure 35 psi, spray rate 14 g/min.) Then, to make a 2:1 S100/L100 mixture, about 194 grams of Eudragit® S100 were dispersed in 914 grams of water and about 98 grams of 0.1 N ammonium hydroxide, and about 97 grams of Eudragit® L100 were dispersed in 457 grams of water and about 33 grams of 0.1 N ammonium hydroxide. The two dispersions were combined with about 203 grams of triethyl citrate, about 147 grams of Plas® II (a blend of plasticizers formulated for use in acrylic coating sold by Emerson Resources Inc., comprising water, glycerol monostearate, triethyl citrate, polysorbate 80, isopropyl alcohol, methyl parabens and propyl parabens) and water (QS to 2,400 grams), and stirred to a uniform mixture. The resulting dispersion was screened through a 60 mesh sieve and spray-coated on to the cores of example I containing 3% (w/w) subcoat of Opadry®. (Approximately, inlet air temp. 36° C., exhaust temp. 32° C., bed temp. 32° C., fan speed 200 cfm, pan speed 8 rpm, air pressure 30 psi, spray rate 18 g/min.) The weight gain of the pH-sensitive Eudragit® coated tablets over the 3% sub-coated tablets was about 8%. Additional tablets were made in the same manner, except that the weight gain (weight of the Eudragit® coated tablets over the weight of the sub-coated tablets) was about 11%.

The tablets were soaked in 0.1 N HCl for 120 minutes, blotted, and then transferred to USP apparatus II in 900 ml of phosphate buffer, at 50 rpm, at a temperature of 37° C. and at a pH of 6.0, 6.8 or 7.2. Samples of 10 ml were withdrawn at designated time points, filtered through a 0.45 micron filter and then analyzed for drug release by UV absorption. There was substantially no release of mesalamine after the 120 minute period the tablets were in 0.1N HCl solution. The average drug release (for 6 tablets) as a function of the time the tablets were in media buffered at pH 6.0, 6.8 or 7.2 is shown in Tables 1 and 2.

Example III

Comparative Example

Cores made substantially in the same manner as described in Example I were coated with a 3% (w/w) subcoat of Opadry® and then spray-coated with an aqueous dispersion containing 294 grams Eudragit® S100, 150 grams 0.1 N ammonium hydroxide, about 203 grams triethyl citrate, about 147 grams Plas® II and water (QS to 2,400 grams) in substantially the same manner as in Example II. The resulting tablets were tested in dissolution apparatus USP II in the same manner as in Example II, and the average drug release (for 6 tablets) as a function of the time the tablets were in media buffered to a pH of 6.0, 6.8 and 7.2 are shown in Table 3. As in Example II, there was substantially no drug release after 120 minutes in 0.1 N HCl.

TABLE 1

(2:1 Eudragit ® S100/L100 coated at 8%)

| Time (min) | % Released in pH 6.0 | % Released in pH 6.8 | % Released in pH 7.2 |
|---|---|---|---|
| 90 | 0.54 (0.90 SD) | 2.2 (2.93 SD) | 71.48 (14.19 SD) |
| 120 | 1.80 (3.15 SD) | 9.63 (6.60 SD) | 84.88 (8.51 SD) |
| 180 | 7.12 (8.34 SD) | 28.14 (11.16 SD) | 94.37 (3.65 SD) |

TABLE 2

(2:1 Eudragit ® S100:L100 coated at 11%)

| Time (min) | % Released in pH 6.0 | % Released in pH 6.8 | % Released in pH 7.2 |
|---|---|---|---|
| 90 | 0.12 (0.08 SD) | — | 63.71 (17.52 SD) |
| 120 | 0.42 (0.31 SD) | 2.50 (4.73 SD) | 79.65 (11.31 SD) |
| 180 | 1.98 (1.89 SD) | 19.81 (10.94 SD) | 95.09 (4.24 SD) |

TABLE 3

(Eudragit ® S100 coated at 8%)

| Time (min) | % Released in pH 6.0 | % Released in pH 6.8 | % Released in pH 7.2 |
|---|---|---|---|
| 90 | — | — | 92.45% (5.76 SD) |
| 120 | — | — | 94.93% (1.82 SD) |
| 180 | — | 9.89% (6.18 SD) | N/A |

Example IV

2:1 Coating at 9%, 10%, 13% and 15%

Cores were manufactured in substantially the same manner as in Example I and coated with 3% subcoat of Opadry® and a pH-sensitive coat of Eudragit® S100 and Eudragit® L100 in a ratio of about 2:1 in substantially the same manner as in Example II, except that the pH-sensitive coating weight gain was about 9%, 10%, 13% and 15%. The tablets were analyzed according to the USP dissolution test for delayed release mesalamine: 120 minutes in 900 mL 0.1 N HCl solution, 37° C. and 100 RPM; followed by 60 minutes in 900 mL solution buffered to a pH of 6.0, 37° C. and 100 RPM; followed by 120 minutes in 900 mL solution buffered to a pH of 7.2, 37° C. and 50 RPM. Samples were withdrawn at designated time points, screened through a 10-micron filter only and analyzed for drug release by UV absorption. Regardless of the coating thickness, the tablets released substantially no drug in the 0.1 N HCl media or in the media buffered to a pH of 6.0. In the media buffered to a pH of 7.2, the tablets released at least 90% of the dosage amount in 120 minutes, regardless of coating thickness. The tablets were then tested by a modified USP dissolution method, wherein in the third stage, the media was buffered to a pH of 6.5 instead of a pH of 7.2. Again the tablets released substantially no drug in solution buffered with 0.1N HCl or at a pH of 6.0. The average (of 6 tablets) amount released in pH 6.5 buffered solution are shown in Table 4 below:

TABLE 4

(2:1 Eudragit ® S100:L100 coated at 9%, 10%, 13%, 15%: dissolution at pH 1(2 hrs), pH 6.0 (1 hr.), pH 6.5 (2 hrs.))

| Time at pH 6.5 (min) | % Released at 9% Coating | % Released at 10% Coating | % Released at 13% Coating | % Released at 15% Coating |
|---|---|---|---|---|
| 0 | — | — | — | — |
| 30 | 5 (4 SD) | 2 (3 SD) | 1 | 1 |
| 60 | 19 (11 SD) | 8 (11 SD) | 2 | 1 |
| 90 | 33 (15 SD) | 16 (18 SD) | 3 | 2 |
| 120 | 40 (14 SD) | 22 (20 SD) | 3 | 3 |

Example V

4:1 Eudragit S100:L100 at 10%, 11%, 14%

Cores were manufactured in essentially the same manner as in Example I and subcoated and coated in essentially the same manner as in Example II, except that the ratio of Eudragit® S100 to L100 was about 4:1, and that the pH-sensitive (Eudragit®) coating weight gain was either about 10%, 11% or 14%. Specifically, to make the 4:1 S100/L100 mixture, about 465 grams of Eudragit® S100 were dispersed in about 2193 grams of water and about 236 grams of 0.1 N ammonium hydroxide, and about 116 grams of Eudragit® L100 were dispersed in about 543 grams of water and about 39 grams of 0.1 N ammonium hydroxide. The two dispersions were combined with about 406 grams of triethyl citrate, about 294 grams of Plas® II and water (QS to 4800 grams), and stirred to a uniform mixture. USP dissolution was performed in the same manner as in Example IV.

Regardless of coating thickness, there was substantially no drug release in solution buffered with 0.1 N HCl or at a pH of 6.0, and in solution buffered to a pH of 7.2, release was at least 90% in 120 minutes. A modified USP test was repeated, wherein the third stage was buffered to a pH of 6.5 instead of a pH of 7.2. Again there was substantially no release in solution buffered with 0.1 N HCl or at a pH of 6.0. The average amount of drug released (for 6 tablets) in pH 6.5 is shown in Table 5. The tablets coated at an 11% weight gain were further tested with a modified USP dissolution test wherein the third stage was buffered to a pH of 6.8, and the average release at pH 6.8 was 7% (15 SD) at 60 minutes, 17% (20 SD) at 90 minutes and 32% (23 SD) at 120 minutes.

TABLE 5

(4:1 Eudragit S100:L100 at 10%, 11% and 14%, dissolution at pH 1 (2 hrs.), pH 6.0 (1 hr.) and pH 6.5 (2 hrs.)

| Time at pH 6.5 (min) | % Released at 10% Coating | % Released at 11% Coating | % Released at 14% Coating |
|---|---|---|---|
| 0 | — | — | — |
| 30 | — | — | — |
| 60 | 1 (1 SD) | — | — |
| 90 | 11 (9 SD) | 1 | 1 |
| 120 | 21 (9 SD) | 1 | 2 |

The above preferred embodiments and examples were given to illustrate the scope and spirit of the present invention. These embodiments and examples will make apparent to those skilled in the art other embodiments and examples. These other embodiments and examples are within the contemplation of the present invention. Therefore the present invention should be limited only by the appended Claims.

The invention claimed is:

1. A delayed release pharmaceutical composition in solid dosage form for oral administration comprising a core comprising a therapeutically effective amount of mesalamine and a pH-sensitive coating comprising a mixture of two different pH sensitive polymers: a first pH sensitive polymer that dissolves at a pH of about 7 or greater and a second pH sensitive polymer that dissolves at a pH of about 6 or greater, wherein the weight ratio of the first pH sensitive polymer to the second pH sensitive polymer ranges from about 2:1 to about 4:1 and the percent weight gain resulting from the addition of said pH sensitive coating ranges from about 10% up to and including 15%, wherein the average percentage amount of mesalamine released from the composition in an USP apparatus II, 900 mL at 37° C., at the conclusion of a three stage dissolution test consisting of a first stage wherein said pharmaceutical composition is stirred for 2 hours at 100 rpm in 0.1N HCl solution, a second stage wherein said composition is stirred for 1 hour at 100 rpm in solution buffered to a pH of 6.0 and a third stage wherein said composition is stirred for 2 hours at 50 rpm, is less than about 20% (w/w) when the third stage is a solution buffered to a pH of 6.5; is about 10% to about 60% (w/w) when the third stage is a solution buffered to a pH of 6.8; and at least about 80% (w/w) when the third stage is a solution buffered to a pH of 7.2.

2. The pharmaceutical composition according to claim 1, wherein the weight ratio of the first pH sensitive polymer to the second pH sensitive polymer ranges from about 2:1 to about 3:1.

3. The pharmaceutical composition according to claim 1, wherein the weight ratio of the first pH sensitive polymer to the second pH sensitive polymer ranges from about 3:1 to about 4:1.

4. A delayed release pharmaceutical composition in solid dosage form for oral administration comprising a core comprising a therapeutically effective amount of mesalamine, and a pH-sensitive coating comprising a mixture of two different polymers: a first pH sensitive polymer that is an anionic copolymer of methacrylic acid and methyl methacrylate, wherein the ratio of free carboxyl groups to ester groups in said first pH sensitive polymer is approximately 1:2, and a second pH sensitive polymer that is different from the first pH sensitive polymer and is an anionic copolymer of methacrylic acid and methyl methacrylate, ratio of free carboxyl groups to ester groups in said second pH sensitive polymer is approximately 1:1, wherein the weight ratio of the first pH sensitive polymer to the second pH sensitive polymer ranges from about 2:1 to about 4:1 and the percent weight gain resulting from the addition of said pH sensitive coating ranges from about 10% up to and including 15%, wherein the average percentage amount of mesalamine released from the composition in USP apparatus II, 900 mL at 37° C., at the conclusion of a three stage dissolution test consisting of a first stage wherein said pharmaceutical composition is stirred for 2 hours at 100 rpm in 0.1N HCl solution, a second stage wherein said pharmaceutical composition is stirred for 1 hour at 100 rpm in solution buffered to a pH of 6.0 and a third stage wherein said pharmaceutical composition is stirred for 2 hours at 50 rpm, is less than about 20% when the third stage is a solution buffered to a pH of 6.5; ranges from about 10% to about 60% when the third stage is a solution buffered to a pH of 6.8; and, is at least about 80% when the third stage is a solution buffered to a pH of 7.2.

5. The pharmaceutical composition according to claim 4, wherein the weight ratio of the first pH sensitive polymer to the second pH sensitive polymer ranges from about 2:1 to about 3:1.

6. The pharmaceutical composition according to claim 4, wherein the weight ratio of the first pH sensitive polymer to the second pH sensitive polymer ranges from about 3:1 to about 4:1.

7. The pharmaceutical composition according to claim 1, further comprising about 1% to about 5% subcoating (w/w) relative to the core comprising a polymeric film former between the core and the pH sensitive coating.

8. The pharmaceutical composition according to claim 7, wherein the weight ratio of the first pH sensitive polymer to the second pH sensitive polymer ranges from about 2:1 to about 3:1.

9. The pharmaceutical composition according to claim 7, wherein the weight ratio of the first pH sensitive polymer to the second pH sensitive polymer ranges from about 3:1 to about 4:1.

10. The pharmaceutical composition according to claim 4, further comprising about 1% to about 5% subcoating (w/w) relative to the core comprising a polymeric film former between the core and the pH sensitive coating.

11. The pharmaceutical composition according to claim 10, wherein the weight ratio of the first pH sensitive polymer to the second pH sensitive polymer ranges from about 2:1 to about 3:1.

12. The pharmaceutical composition according to claim 10, wherein the weight ratio of the first pH sensitive polymer to the second pH sensitive polymer ranges from about 3:1 to about 4:1.

13. The pharmaceutical composition according to claim 7, wherein the polymeric film former is hydroxypropylmethylcellulose.

14. The pharmaceutical composition according to claim 10, wherein the polymeric film former is hydroxypropylmethylcellulose.

15. A delayed release oral solid dosage form comprising a core comprising a therapeutically effective amount of mesalamine and a pH-sensitive coating applied to said core, said pH-sensitive coating comprising a mixture of a first pH sensitive polymer that dissolves at a pH of about 7 or greater and a second pH sensitive polymer that dissolves at a pH of about 6 or greater, the weight ratio of the first pH sensitive polymer to the second pH sensitive polymer being from about 2:1 to about 4:1 and the percent weight gain resulting from the addition of said pH sensitive coating is from about 10% up to and including 15%, whereby the average percentage amount of mesalamine released from the composition in a USP apparatus II, 900 mL at 37° C., at the conclusion of a three stage dissolution test consisting of a first stage wherein said pharmaceutical composition is stirred for 2 hours at 100 rpm in 0.1N HCl solution, a second stage wherein said composition is stirred for 1 hour at 100 rpm in solution buffered to a pH of 6.0 and a third stage wherein said composition is stirred for 2 hours at 50 rpm, is less than about 20% (w/w) when the third stage is a solution buffered to a pH of 6.5; is about 10% to about 60% (w/w) when the third stage is a solution buffered to a pH of 6.8; and at least about 80% (w/w) when the third stage is a solution buffered to a pH of 7.2.

* * * * *

UNITED STATES PATENT AND TRADEMARK OFFICE
CERTIFICATE OF CORRECTION

| | | |
|---|---|---|
| PATENT NO. | : 7,964,215 B1 | |
| APPLICATION NO. | : 11/604434 | |
| DATED | : June 21, 2011 | |
| INVENTOR(S) | : Madurai Gurusamy Ganesan et al. | |

It is certified that error appears in the above-identified patent and that said Letters Patent is hereby corrected as shown below:

Please correct the following:

a) Column 12, line 15 in claim 1,
"37°C.," should read --37°C-- b) Column 12, line 44 in claim 4,
"methacrylate, ratio" should read --methacrylate, wherein the ratio-- c) Column 12, line 52 in claim 4,
"37°C.," should read --37°C-- d) Column 14, line 19 in claim 15,
"37°C.," should read --37°C--

Signed and Sealed this
Ninth Day of August, 2011

David J. Kappos
*Director of the United States Patent and Trademark Office*